(12) United States Patent
Lanze et al.

(10) Patent No.: US 6,414,198 B1
(45) Date of Patent: Jul. 2, 2002

(54) METHOD FOR PRODUCING BISPHENOL-A

(75) Inventors: Rolf Lanze; Rainer Neumann, both of Krefeld; Steffen Kühling, Meerbusch; Frieder Heydenreich, Düsseldorf; Tony Van Osselaer, Krefeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/868,806

(22) PCT Filed: Dec. 14, 1999

(86) PCT No.: PCT/EP99/09917

§ 371 (c)(1),
(2), (4) Date: Jun. 21, 2001

(87) PCT Pub. No.: WO00/39060

PCT Pub. Date: Jul. 6, 2000

(30) Foreign Application Priority Data

Dec. 24, 1998 (DE) .......................... 198 60 144

(51) Int. Cl.[7] .............................................. C07C 37/68
(52) U.S. Cl. ........................................................ 568/724
(58) Field of Search ........................................ 568/724

(56) References Cited

U.S. PATENT DOCUMENTS

| | | | |
|---|---|---|---|
| 2,775,620 A | | 12/1956 | Williamson |
| 5,629,457 A | | 5/1997 | Zhang et al. |
| 5,783,733 A | * | 7/1998 | Kissinger .................... 568/724 |
| 5,785,823 A | * | 7/1998 | Meurer et al. .............. 568/724 |

FOREIGN PATENT DOCUMENTS

| | | |
|---|---|---|
| EP | 0 342 758 | 5/1995 |
| EP | 0 523 931 | 10/1996 |

\* cited by examiner

*Primary Examiner*—Alan Siegel
(74) *Attorney, Agent, or Firm*—Joseph C. Gil; Aron Preis; James R. Franks

(57) ABSTRACT

A process of preparing bisphenol A having low residual contents of oxygen and phenol is described. The process involves: (a) melting mixed crystals of bisphenol A and phenol under a nitrogen atmosphere at a temperature of 100° C. to 120° C.; (b) feeding continuously the melt formed in step (a) into the top of a distillation unit under conditions of 120° C. to <160° C. and a pressure of >80 mbar to 200 mbar; (c) feeding contemporaneously with step (b) nitrogen into the bottom of the distillation unit; (d) allowing the melted feed material and the nitrogen feed to contact each other within the distillation unit, thereby forming a concentrated melt material having (i) a phenol content reduced to 10 to 25 wt. %, and (ii) a reduced oxygen content (e.g., an oxygen content of <1 ppm); and (e) optionally passing a stream of nitrogen through the concentrated melt material under conditions of at least atmospheric pressure, 180° C. to 220° C. and a nitrogen partial pressure of 1 to 1.5 bar, thereby removing residual phenol from the concentrated melt material (e.g., resulting in a phenol content of <50 ppm). The melted material having reduced oxygen and phenol contents may be further processed, for example, into pellets.

8 Claims, No Drawings

METHOD FOR PRODUCING BISPHENOL-A

CROSS REFERENCE TO RELATED PATENT APPLICATIONS

The present patent application is a 371 of International Application No. PCT/EP99/09917, filed Dec. 14, 1999, which was published in German as International Patent Publication No. WO 00/39060 on Jul. 6, 2000, which is entitled to the right of priority of German Patent Application No. 198 60 144.1, filed Dec. 24, 1998.

FIELD OF THE INVENTION

The present invention relates to a process for the preparation of a bisphenol A which is light in colour and has low residual contents of oxygen and phenol, starting from mixed crystals of bisphenol A and phenol.

BACKGROUND OF THE INVENTION

EP-A 523 931 discloses a process wherein an adduct of bisphenol A and phenol is melted in an atmosphere containing 50 ppm at most, preferably 10 ppm at most, of oxygen. The melting is carried out at 115° C. to 180° C., preferably 120° C. to 150° C., at a pressure of 1.0 to 5.0 atm., preferably 1.0 to 1.9 atm. Phenol is removed from the melt by evaporation. The temperature is 160° C. to 200° C., preferably 170° C. to 185° C.; the pressure is at most 100 torr (133 mbar), preferably 5 to 40 torr (7 to 53 mbar). Preferably, the bulk of the phenol is first of all distilled off in a downflow evaporator at 160° C. to 185° at 20 to 80 mbar to a residual content of 1 to 5wt. %, and the residual phenol is then removed by steam at 20 mbar at most and at 170° C. to 185° C. The ratio of steam:BPA is from 1:50 to 1:5, preferably 1:25 to 1:10. In order to effect the separation of the phenol from the BPA as far as possible with the exclusion of oxygen, it is proposed that all the surfaces of the apparatus used which are in contact with the product be freed from oxygen by means of an organic solvent, preferably phenol. The best bisphenol products obtained from the directions given in EP-A 523 931 have colour values (APHA) of 10.

SUMMARY OF THE INVENTION

A process has now been found whereby products having even better colour values can be obtained, and which moreover renders unnecessary the elaborate washing step for removing traces of oxygen from the apparatus.

The invention provides a process for the preparation of bisphenol A, wherein a mixed crystallisate of bisphenol A and phenol is melted at temperatures of 100° C. to 120° C., the melt is then rendered inert with nitrogen and fed in continuously at the top of a first distillation unit wherein, at temperatures of 120° C. to <160° C., preferably 120° C. to 157° C., and at pressures of >80 to 200 mbar, preferably 85 to 200 mbar, particularly preferably 85 to 120 mbar, the phenol content of the melt is decreased to 10 to 25 wt. %, and at the same time 0.5 to 50 vol. %, preferably 2 to 20 vol. %, of nitrogen, based on the volume of introduced melt, is passed in via the bottom of the distillation unit, and the concentrated melt freed from oxygen is subsequently freed from residual phenol at temperatures of 180° C. to 220° C. and at 1 to 1.5 bar nitrogen partial pressure.

The invention also provides a process for the preparation of melts containing 75 to 90 wt. % bisphenol A and 10 to 25 wt. % phenol and having an oxygen content of <1 ppm, preferably <100 ppb, particularly preferably <10 ppb, wherein mixed crystals containing 60 wt. % bisphenol A and 40 wt. % phenol are melted at temperatures of 100° C. to 120° C., the melt is then rendered inert with nitrogen and fed in continuously at the top of a distillation unit wherein, at temperatures of 120° C. to <160° C., preferably 120° C. to 157° C., and at pressures of >80 to 200 mbar, preferably 85 to 200 mbar, particularly preferably 85 to 120 mbar, the phenol content of the melt is decreased to 10 to 25 wt. %, and at the same time 0.5 to 50 vol. % of nitrogen, preferably 2 to 20 vol. %, of nitrogen, based on the volume of introduced melt, is passed in via the bottom of the distillation unit.

DETAILED DESCRIPTION OF THE INVENTION

In the process according to the invention, mixed crystallisates of bisphenol A and phenol are used as educt, preferably those having a bisphenol content of 60 wt. % and a phenol content of 40 wt. %. Such mixed crystallisates are obtained, for example, during the acid-catalysed reaction of phenol and acetone, which is described, for example, in U.S. Pat. No. 2,775,620 or EP-A 342 758. As a rule, the preparation is conducted as a continuous process. The mixed crystallisate of bisphenol A and phenol obtained as product is separated off by filtering the mother liquor, for example, by means of a rotary filter. The filter cake can then be washed with phenol in order to remove adhering impurities. The resulting cake of mixed crystals can be used as educt in the process according to the invention.

In a first step, the mixed crystallisate is melted at temperatures of 100° C. to 120° C. This is carried out in a nitrogen atmosphere. Because of the low reactivity of bisphenol with oxygen at these low temperatures, it is not necessary here to ensure that oxygen is totally excluded. Oxygen contents of 0.1 to 2 vol. % can therefore be tolerated in the atmosphere during the melting process. It is advisable to collect the melt in a container rendered inert with nitrogen.

The melt, which may still contain dissolved oxygen, is then fed in continuously at the top of a distillation unit. It is important that as large an exchanging surface as possible be produced in this distillation unit. Accordingly, a packed column, packing column, tray column or a downflow evaporator, film evaporator or an evaporator with forced circulation is preferably used for this step.

In the distillation unit, at temperatures of 120° C. to <160° C., preferably 120° C. to 157° C., and at pressures of >80 to 200 mbar, preferably 85 to 200 mbar, particularly preferably 85 to 120 mbar, the phenol content of the melt is decreased to 10 to 25 wt. %, and at the same time 0.5 to 50 vol. % of nitrogen, preferably 2 to 20 vol. %, of nitrogen, based on the volume of introduced melt, is passed in via the bottom of the distillation unit.

It is important in this step that melt and nitrogen be passed through in countercurrent, in order to discharge the dissolved oxygen in the melt as completely as possible. Here the removal of the oxygen is assisted by the evaporation of phenol and by the lowered pressure. Under the given conditions, the stream of nitrogen assists the removal of oxygen without lowering the partial pressure of the phenol. In the first distillation unit, dissolved oxygen is removed from the melt under mild conditions, leaving a residual content of <1 ppm. Melts having oxygen contents of <100 ppb and even <10 ppb can be obtained by optimal selection of the conditions. Moreover, no losses of bisphenol A occur under the conditions of pressure and temperature established in this step; such losses would necessitate an additional processing step in which bisphenol A is recovered from the vapour phase.

In a further step, the melt thus obtained can then be freed from residual phenol at temperatures of 180° C. to 220° C., preferably 185° C. to 195° C., and nitrogen partial pressures of 1 to 1.5 bar, preferably 1 to 1.1 bar. In the course of this, a stream of nitrogen is passed through the melt in order to assist the removal of the phenol ("stripping"). Here the proportion of gas to melt is preferably 10 to 1000 m$^3$ nitrogen per t of melt. The units employed for the removal of phenol are familiar to the person skilled in the art; for example, a packed column operated by flooding can be used for this.

The removal of phenol at atmospheric pressure enables the melt to be rendered inert better than is possible by the desorption under vacuum conditions as described in EP-A 523 931 and has the advantage, moreover, that no oxygen can flow into the apparatus in the event of leakages. Furthermore, the apparatus is rendered inert by the stream of nitrogen and any oxygen which may be adsorbed onto the surfaces in contact with the product is swept out, which renders washing of these surfaces with organic solvent superfluous. The bisphenol A thus obtained has a residual phenol content of 50 ppm at most and shows colour values (measured in accordance with ASTM D 1686) of less than 10.

The melt can subsequently be processed directly into pellets or used for the preparation of sodium bisphenolate solutions for polycarbonate production. Polycarbonates produced from bisphenol A obtained by the process according to the invention have a lower Yellowness Index (Y.I.) than that of the products of prior art. The bisphenol A obtained by the process according to the invention can also be used with advantage for the preparation of epoxy resins.

EXAMPLES

Example 1

A melt which contained 60 wt. % bisphenol A and 40 wt. % phenol, and in which oxygen was still dissolved, was fed in continuously at the top of a packed column in a quantity of 1 t/h. The temperature at the bottom of the column was 145° C.; the pressure at the top of the column was 100 mbar. 50 l of nitrogen per hour was passed continuously to the downflow evaporator of the column in countercurrent to the flow of product. In a subsequent desorption step, at a melting temperature of 190° C., the mixture discharged from the column (75 wt. % bisphenol A, 25 wt. % phenol) was freed from phenol by means of 225 m$^3$ of nitrogen per hour. The phenol contained in the circulating nitrogen was condensed. 750 l of the recirculated nitrogen was exchanged per hour. The oxygen content of the circulating nitrogen was 0.4 ppm. A BPA melt was obtained which was low in phenol (50 ppm) and had a colour value of 8 Hazen (measured in accordance with ASTM D 1686).

Comparison Example 1

The procedure was carried out as in Example 1, but the continuous supply of nitrogen to the downflow evaporator was dispensed with. The oxygen content of the circulating nitrogen was 5 ppm. A BPA melt was obtained which was low in phenol (50 ppm) and had a colour value of 12 Hazen.

Comparison Example 2

A melt which contained 60 wt. % bisphenol A and 40 wt. % phenol, and in which oxygen was still dissolved, was passed continuously in a quantity of 1 t/h directly into the desorption step and, at a melting temperature of 190° C., was freed from phenol by means of 225 m$^3$ of nitrogen per hour. The phenol contained in the circulating nitrogen was condensed. 750 l of the recirculated nitrogen was exchanged per hour. The oxygen content of the circulating nitrogen was 5 ppm. A BPA melt was obtained which had a phenol content of 250 ppm and had a colour value of 14 Hazen.

Comparison Example 3

The procedure was carried out as in Comparison Example 2, but the phenol desorption was operated at a melting temperature of 200° C. in order to lower the phenol content further. A BPA melt was obtained which was low in phenol (50 ppm) and had a colour value of 18 Hazen.

What is claimed is:

1. A process of preparing bisphenol A having low residual contents of oxygen and phenol comprising:
    (a) melting mixed crystals of bisphenol A and phenol under a nitrogen atmosphere at a temperature of 100° C. to 120° C.;
    (b) feeding continuously the melt formed in step (a) into the top of a distillation unit under conditions of 120° C. to less than 160° C. and a pressure of greater than 80 mbar to 200 mbar;
    (c) feeding contemporaneously with step (b) 0.5 to 50 vol. % of nitrogen, based on the volume of introduced melt, into the bottom of the distillation unit;
    (d) allowing the melted feed material and the nitrogen feed to contact each other within the distillation unit, thereby forming a concentrated melt material having,
        (i) a phenol content reduced to 10 to 25 wt. %, and
        (ii) a reduced oxygen content; and
    (e) removing the concentrated melt material of step (d) from the bottom of the distillation unit and passing a stream of nitrogen through the removed concentrated melt material under conditions of at least atmospheric pressure, 180° C. to 220° C. and a nitrogen partial pressure of 1 to 1.5 bar, thereby further reducing the residual phenol content of the concentrated melt material.

2. The process of claim 1 wherein the mixed crystals of bisphenol A and phenol melted in step (a) contain 60 percent by weight of bisphenol A and 40 weight percent of phenol, based on the total weight of the mixed crystals.

3. The process of claim 1 wherein the oxygen content (ii) of the concentrated melt material of step (d) is less than 1 ppm.

4. The process of claim 1 wherein the phenol content of the concentrated melt material of step (e) is less than 50 ppm.

5. The process of claim 1 wherein the proportion of nitrogen gas to concentrated melt material in step (e) is 10 to 1000 m$^3$ of nitrogen per ton of concentrated melt material.

6. The process of claim 1 wherein the concentrated melt material of step (e) is further processed into the form of pellets.

7. A process of preparing bisphenol A having low residual contents of oxygen and phenol comprising:
    (a) melting mixed crystals comprising 60 wt. % of bisphenol A and 40 wt. % of phenol under a nitrogen atmosphere at a temperature of 100° C. to 120° C.;
    (b) feeding continuously the melt formed of step (a) into the top of a distillation unit under conditions of 120° C. to less than 160° C. and a pressure of greater than 80 mbar to 200 mbar;
    (c) feeding contemporaneously with step (b) 0.5 to 50 vol. % of nitrogen, based on the volume of introduced melt, into the bottom of the distillation unit;
    (d) allowing the melted feed material and the nitrogen feed to contact each other within the distillation unit, thereby forming a concentrated melt material having, (i) a phenol content of 10 to 25 wt. %,
(ii) a bisphenol A content of 75 to 90 wt. %, and
(iii) an oxygen content of less than 1 ppm; and
(e) removing the concentrated melt material of step (d) from the bottom of the distillation unit.

8. The process of claim 7 wherein the concentrated melt material of step (e) is further processed into the form of pellets.

* * * * *